United States Patent

Vaitekunas et al.

[11] Patent Number: 5,993,458
[45] Date of Patent: Nov. 30, 1999

[54] METHOD OF ULTRASONICALLY EMBEDDING BONE ANCHORS

[75] Inventors: Jeffrey J. Vaitekunas, West Chester; Mary E. Mootoo, Cincinnati; Narinderjit S. Sambi, Mason, all of Ohio; Navneet T. Sharma, Bridgewater, N.J.

[73] Assignee: Ethicon, Inc., Somerville, N.J.

[21] Appl. No.: 09/104,789

[22] Filed: Jun. 25, 1998

[51] Int. Cl.⁶ ..................................................... A61B 17/58
[52] U.S. Cl. ............................................. 606/104; 606/73
[58] Field of Search ................................. 606/53, 72, 73, 606/75, 86, 99, 104

[56] References Cited

U.S. PATENT DOCUMENTS

| | | | |
|---|---|---|---|
| 5,019,083 | 5/1991 | Klapper et al. | 606/99 |
| 5,318,570 | 6/1994 | Hood et al. | 606/99 |
| 5,411,523 | 5/1995 | Goble | 606/232 |
| 5,413,578 | 5/1995 | Zahedi | 606/86 |
| 5,417,712 | 5/1995 | Whittaker et al. | 606/232 |
| 5,441,502 | 8/1995 | Bartlett | 606/104 |
| 5,449,370 | 9/1995 | Vaitekunas | 606/169 |
| 5,520,696 | 5/1996 | Wenstrom, Jr. | 606/104 |
| 5,522,845 | 6/1996 | Wenstrom, Jr. | 606/232 |
| 5,662,658 | 9/1997 | Wenstrom, Jr. | 606/104 |

FOREIGN PATENT DOCUMENTS

| | | |
|---|---|---|
| 9-173344 | 7/1997 | Japan. |
| 2072801 | 2/1997 | Russian Federation. |

*Primary Examiner*—Michael Buiz
*Assistant Examiner*—Julian W. Woo
*Attorney, Agent, or Firm*—Bernard E. Shay

[57] ABSTRACT

Bone anchors, after insertion into bone, are designed to remain in place and provide a platform for holding tissue. A method of ultrasonically embedding bone anchors into bone without pre-drilling an anchor receiving hole into the bone has been developed. Also described is an improved bone anchor embedding method utilizing ultrasonic energy to reduce insertion force, whereby the bone anchor and embedding device can be formed very small, (e.g. on the order of 2 to 5 millimeters in diameter). In an embodiment of the present invention, a method of bone anchor embedding utilizing ultrasonic energy is used to insert a bone anchor into a pre-drilled hole, wherein the hole in the bone may be smaller in diameter than the diameter of the bone anchor.

10 Claims, 7 Drawing Sheets

METHOD OF ULTRASONICALLY EMBEDDING BONE ANCHORS

This application is related to the following copending patent applications: Ser. No. 08/948,952; filed Oct. 10, 1997 [Applicant Docket No. END-424]; Ser. No. 08/808,637; filed Feb. 28, 1997 [Applicant Docket No. END-396]; Ser. No. 09/104,612; filed, Jun. 25, 1998 [Applicant Docket No. MIT-0119]; and Ser. No. 09/104,648; filed, Jun. 25, 1998 [Applicant Docket No. MIT-0132], which are hereby incorporated herein by reference.

FIELD OF THE INVENTION

The present invention relates, in general, to a method of attaching a bone anchor to a bone and, more particularly, to a method of attaching a bone anchor utilizing ultrasonic energy.

BACKGROUND OF THE INVENTION

Ultrasonic surgical instruments are finding increasingly widespread applications in surgical procedures by virtue of the unique performance characteristics of such instruments. Depending on specific instrument configurations and operational parameters, ultrasonic surgical instruments can provide increased control while significantly reducing surgeon effort and fatigue. Ultrasonic surgical instruments can help reduce surgeon effort during bone shaving, and reduce the force required to penetrate tissue, for example, when inserting a trocar through the abdominal wall of a patient.

Ultrasonic trocar obturators may be used to reduce the force necessary to penetrate the abdominal wall during laparoscopic surgery. Such a device is disclosed in U.S. Pat. No. 5,449,370, which describes using ultrasonic energy to assist in the insertion of a trocar obturator and cannula into a body cavity through, for example, the abdominal wall of a human being, providing access to internal organs or other tissue.

Ultrasonic devices for removing bone cement tubes during prosthesis replacements have been developed. U.S. Pat. Nos: 5,019,083; 5,413,578; and 5,318,570 describe the need to reduce the force necessary when removing bone cement used for prosthesis fixation, and to increase the surgeons control during the removal process. The ultrasonic devices described in U.S. Pat. Nos. 5,019,083; 5,413,578; and 5,318,570 are designed to loosen, or fracture, cement while leaving the bone intact.

Bone anchors and bone anchor insertion devices have been described in, for example, U.S. Pat. No. 5,522,845, which describes a bone anchor and a bone anchor insertion tool. In U.S. Pat. No. 5,522,845, a bone anchor insertion tool is used to insert a specially adapted bone anchor into a pre-drilled hole. The bone anchor described in U.S. Pat. No. 5,522,845 includes a suture placed through a bore in the body of the bone anchor. The insertion device funnels and protects the suture from damage during the insertion of the bone anchor into the bone. The bone anchor described in U.S. Pat. No. 5,522,845 also includes barbs protruding from its body. The barbs are used to retain the anchor in the pre-drilled hole. The pre-drilled hole is designed to have a diameter larger than the diameter of the maximum cross-section of the bone anchor in order to reduce the insertion force required to insert the anchor into the bone.

Bone anchors, after insertion into bone, are designed to remain in place and provide a platform for holding tissue. Bone anchors which include a wide spaced multiple turn thread on the outer surface of the bone anchor body have been described in, for example, U.S. Pat. No. 5,411,523. The teaching of U.S. Pat. No. 5,411,523 provides a strong union, or purchase, between the bone and the anchor whereby the anchor is driven clockwise to insert the bone anchor into a pre-drilled hole (i.e. a right-handed screw thread). Counter-clockwise rotation is used to disconnect the bone anchor from the insertion device. Additionally U.S. Pat. No. 5,411,523 describes a bone anchor with a center longitudinal screw thread hole also containing right-handed screw threads.

Bone anchor insertion devices have also been described in, for example, U.S. Pat. No. 5,662,658, which describes a bone anchor and driver contained within a sleeve. The sleeve is connected to a handle with an actuator operative from the handle. In U.S. Pat. No. 5,662,658 the actuator is used to move the driver axially and insert the bone anchor into a previously drilled hole.

It would be advantageous to provide a method of ultrasonically embedding bone anchors into bone without pre-drilling an anchor receiving hole into the bone. It would also be advantageous to provide a method of ultrasonically embedding a bone anchor whereby the removal of the ultrasonic embedding device from the bone anchor sets the bone anchor into the bone. It would be advantageous to provide an improved bone anchor embedding method which utilizes ultrasonic energy to reduce insertion force, whereby the bone anchor and embedding device can be formed very small, (e.g. on the order of 2 to 5 millimeters in diameter). It would further be advantageous to provide a method of bone anchor embedding utilizing ultrasonic energy to insert a bone anchor into a pre-drilled hole, wherein the hole in the bone may be smaller in diameter than the diameter of the bone anchor.

SUMMARY OF THE INVENTION

A method of ultrasonically embedding bone anchors into bone is described, comprising the steps of providing an ultrasonic bone anchor embedding device including a bone anchor, placing the ultrasonic bone anchor against a bone, energizing the bone anchor embedding device causing it to vibrate ultrasonically, embedding the bone anchor into bone, and then removing the bone anchor embedding device from the bone anchor.

In another embodiment, a method of embedding bone anchors into bone is described, including the steps of providing an ultrasonic bone anchor embedding device including a bone anchor, drilling a pilot hole in a bone where the pilot hole diameter is less than or equal to the bone anchor diameter, placing the ultrasonic bone anchor in contact with the pilot hole, energizing the bone anchor embedding device causing it to vibrate ultrasonically, embedding the bone anchor into bone, and then removing the bone anchor embedding device from the bone anchor.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
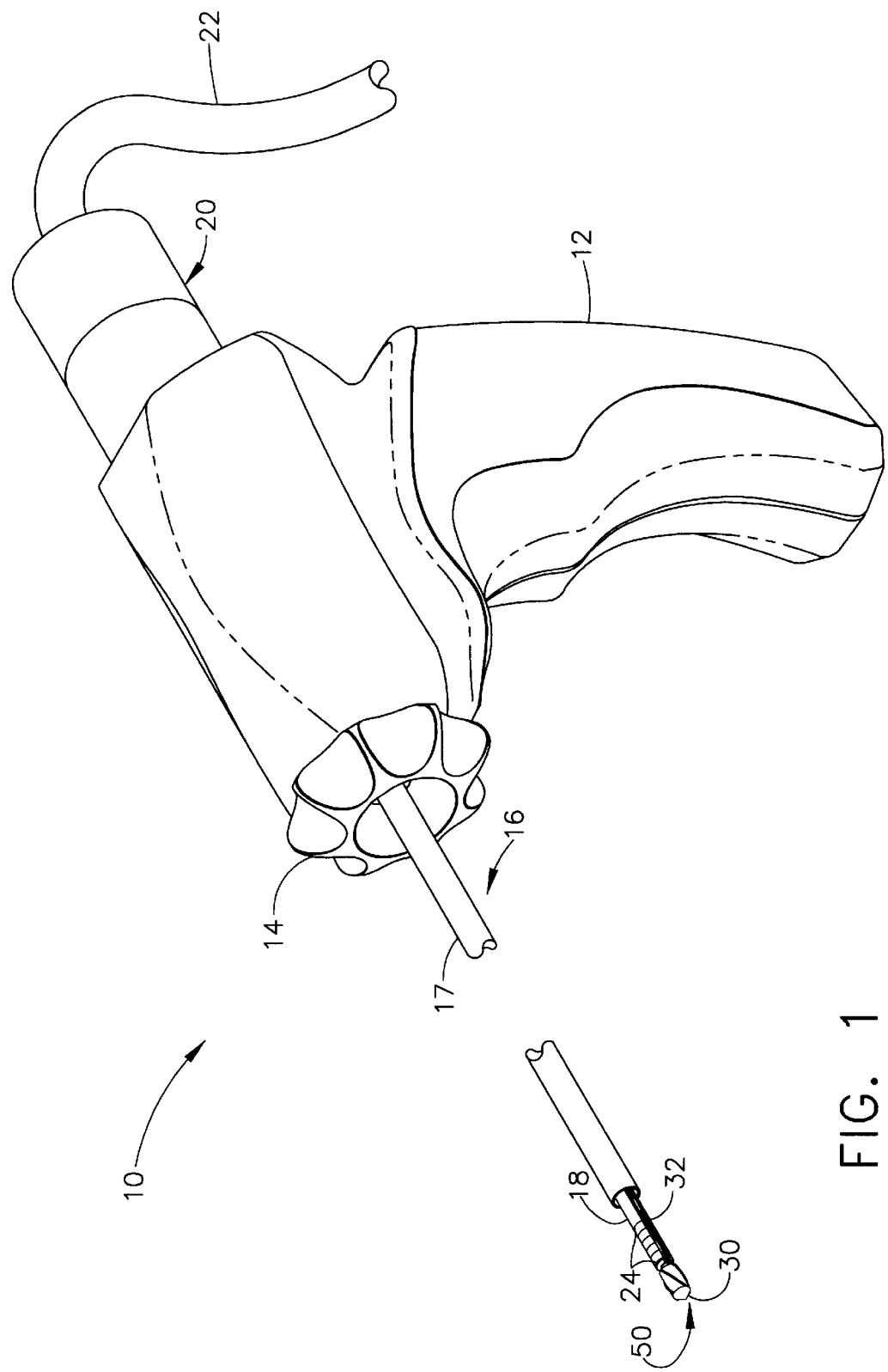
FIG. 1 is an isometric view illustrating an ultrasonic bone anchor embedding device in accordance with the present invention, including an ultrasonic transducer, waveguide assembly, and ultrasonic bone anchor.

FIG. 1 is an isometric view illustrating an ultrasonic embedding device 10 in accordance with the present invention, including an ultrasonic transducer assembly 20, waveguide assembly 16, and ultrasonic bone anchor 30. Waveguide assembly 16 comprises an ultrasonic waveguide 18 which may include depth indicators 24, an outer sheath 17, and rotation knob 14. Ultrasonic bone anchor 30, which may include a suture 32, is connected to ultrasonic waveguide 18 of waveguide assembly 16 by, for example, screw threads such as those illustrated in FIG. 3.

Figure 1A:
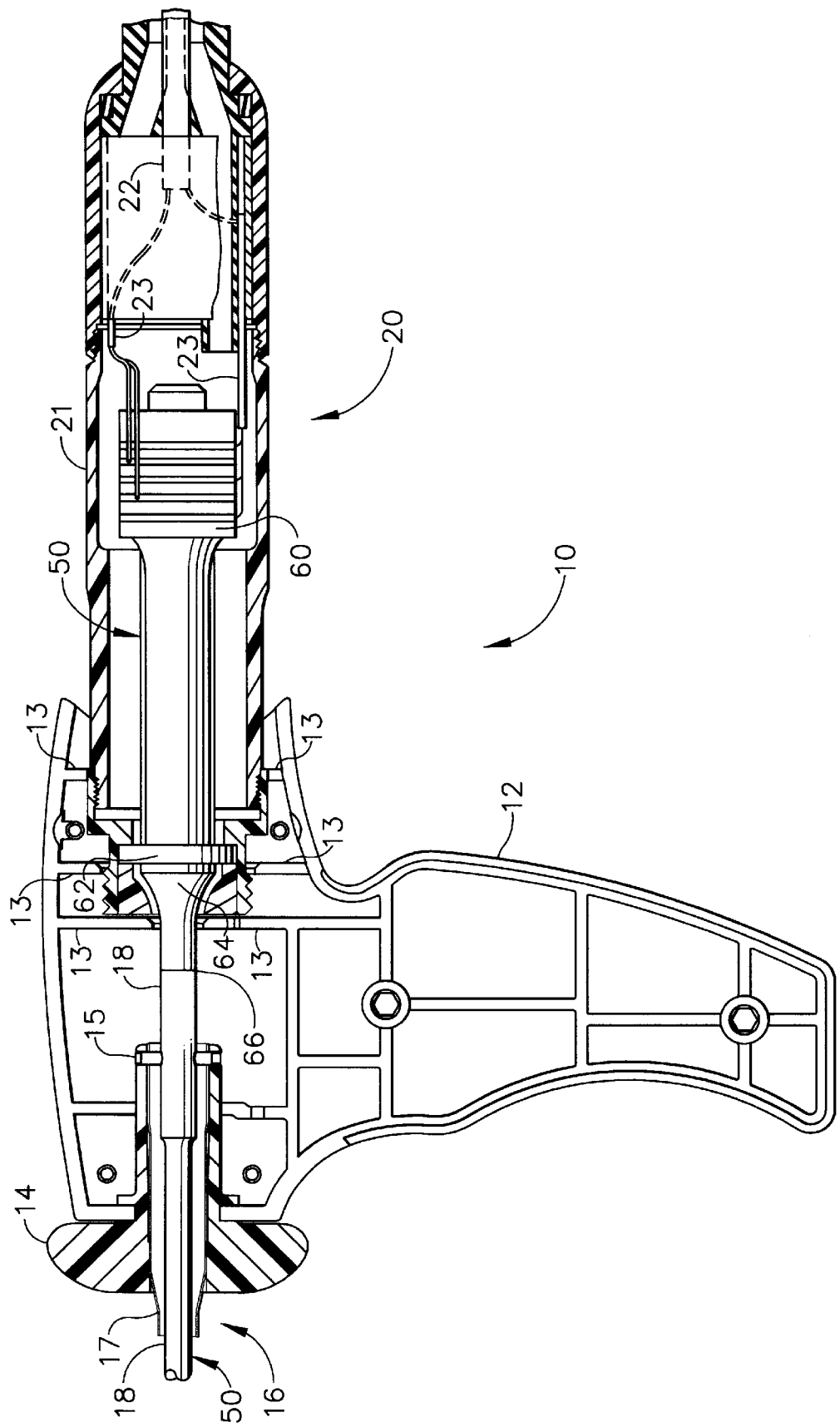
FIG. 1A is a fragmentary sectional view illustrating an ultrasonic bone anchor embedding device in accordance with the present invention, including an ultrasonic transducer, housing, and a proximal portion of a waveguide assembly.

FIG. 1A is a fragmentary sectional view illustrating ultrasonic embedding device 10 in accordance with the present invention, including an ultrasonic transducer assembly 20, device housing 12, and the proximal portion of waveguide assembly 16. Device housing 12 includes transducer support ribs 13 which rotatably support transducer assembly 20 within device housing 12. Transducer assembly 20 is inserted into device housing 12 and attached to waveguide assembly 16 similarly to the ultrasonic clamp coagulator apparatus described in U.S. Pat. application Ser. No. 08/948,952 previously incorporated herein by reference. Ultrasonic transducer stack 60 is located within transducer housing 21 by stack mount 62. Velocity transformer 64 is positioned between stack 60 and waveguide/stack coupler 66. Wires 23 from transducer cable 22 conduct electrical energy to stack 60 from a signal generator ( not shown). A suitable ultrasonic signal generator is available from Ethicon Endo-Surgery, Inc. as make ULTRACISION® and model GEN01. Waveguide 18, outer sheath 17, and rotation knob 14 are rigidly connected by waveguide pin 15, as described in application Ser. No. 08/808,637 previously incorporated herein by reference.

Figure 2:
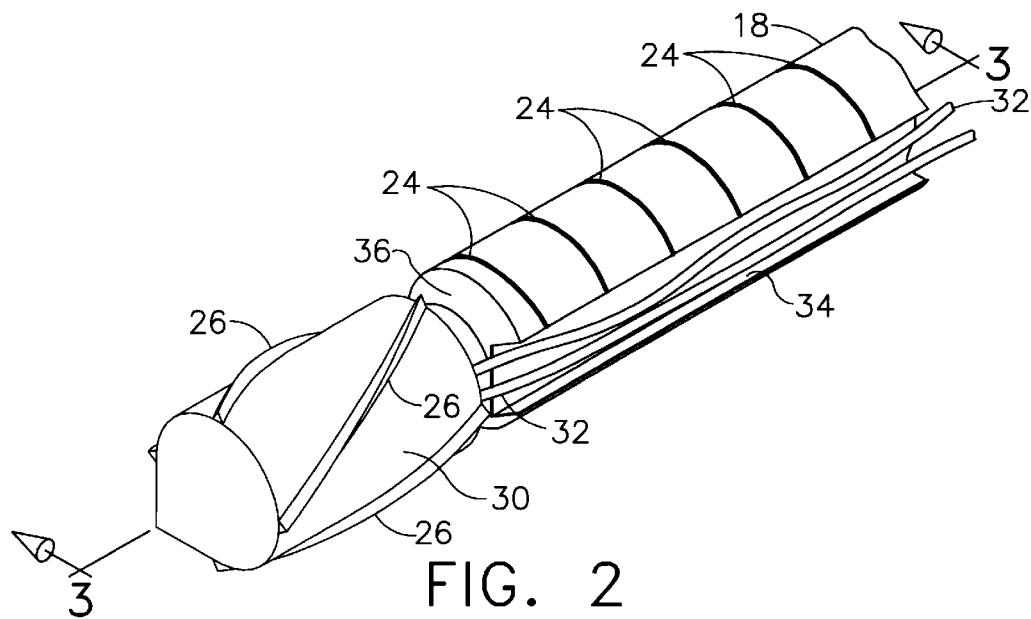
FIG. 2 is an enlarged, fragmentary, isometric view of the distal end of the ultrasonic waveguide assembly illustrated in FIG. 1, including an ultrasonic bone anchor, suture, and waveguide.

FIG. 2 is an enlarged, fragmentary, isometric view of the distal end of the ultrasonic waveguide assembly 16 illustrated in FIG. 1, including an ultrasonic bone anchor 30, suture 32, and ultronic waveguide 18. Anchor threads 26 are positioned on the outer surface of ultrasonic bone anchor 30. In the embodiment of FIG. 1, anchor threads 26 are raised regions arranged in a left handed screw thread. Suture 32 is connected to ultrasonic bone anchor 30 and extends from proximal face 33 (Shown in FIG. 3), through suture attachment recess 36 and suture groove 34 in ultrasonic waveguide 18. Depth indicators 24 are spaced along the distal end of ultrasonic waveguide 18.

Figure 3:
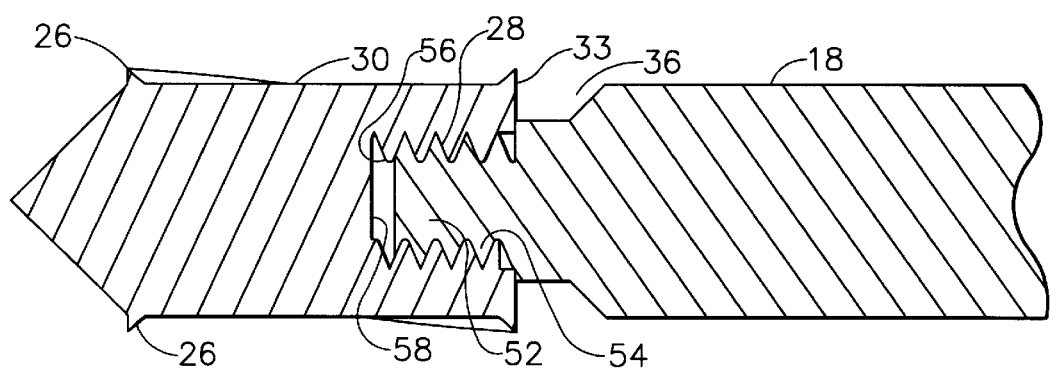
FIG. 3 is an enlarged sectional view taken along line 3—3 of FIG. 2, illustrating a threaded connection between the end of the ultrasonic waveguide assembly and the bone anchor.

FIG. 3 is an enlarged sectional view taken along line 3—3 of FIG. 2. FIG. 3 illustrates the threaded connection between the distal end of ultrasonic waveguide 18 and ultrasonic bone anchor 30. Anchor threads 26, which are arranged in a left handed screw thread, lie on the outer surface of ultrasonic bone anchor 30. Ultrasonic bone anchor 30 contains threaded connector 28 which may be formed in a right handed screw thread. Threaded connector 28 includes anchor recess 58 in ultrasonic bone anchor 30, female threads 56 formed within anchor recess 58, waveguide stud 52 at the distal end of ultrasonic waveguide 18, and male threads 54 formed on waveguide stud 52. Ultrasonic bone anchor 30 is shown screwed onto ultrasonic waveguide 18 utilizing threaded connector 28.

Figure 4:
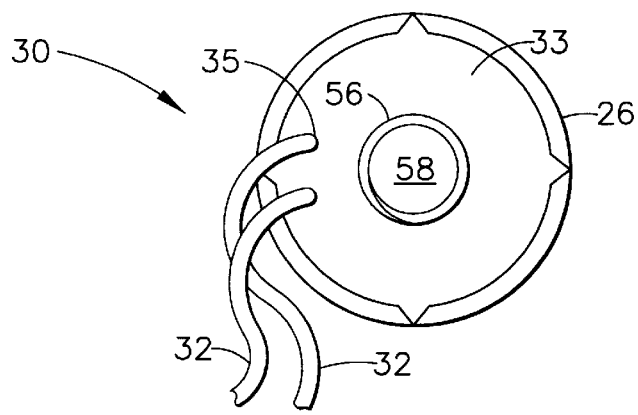
FIG. 4 is an enlarged view of the proximal face of an ultrasonic bone anchor illustrating the location of a threaded bone anchor connector and suture attachment.

FIG. 4 is an enlarged view of the anchor proximal face 33 of ultrasonic bone anchor 30. FIG. 4 illustrates the anchor face suture location 35. Anchor recess 58 is centrally located in the anchor proximal face 33. Suture 32 is illustrated attached radially from anchor recess 58 at anchor face suture location 35. Anchor face suture location 35 is located such that suture 32 lies within suture attachment recess 36 ( shown in FIG. 2) when ultrasonic bone anchor 30 is attached to ultrasonic waveguide 18 (FIG. 3). Suture 32 may be attached to ultrasonic bone anchor 30 by standard means known in the art, for example, gluing.

Figure 5:
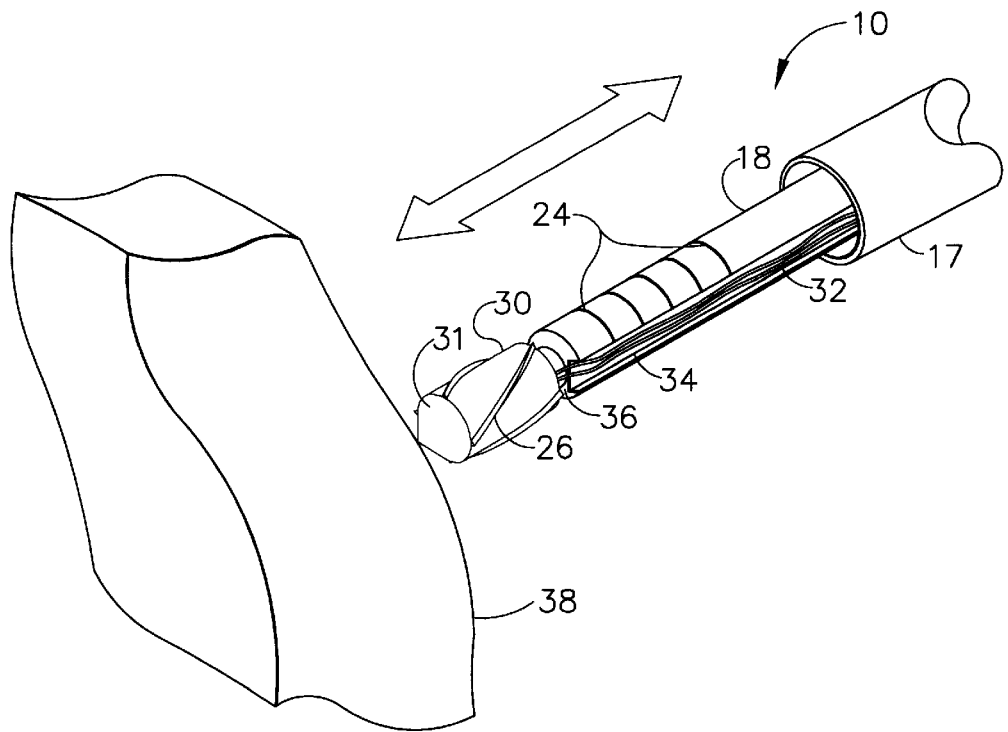
FIG. 5 is an enlarged, fragmentary, isometric view of the distal end of the ultrasonic bone anchor embedding device containing an ultrasonic bone anchor approaching a bone.

Operation of the illustrated embodiment of the invention may be understood by referring to FIGS. 5–8. FIG. 5 is an enlarged, fragmentary, isometric view of the distal end of the ultrasonic embedding device 10 including an ultrasonic bone anchor 30 which is illustrated approaching a bone mass 38. Bone anchor tip 31 of ultrasonic bone anchor 30 is illustrated in contact with bone mass 38. Suture 32 lies within suture groove 34 of ultrasonic waveguide 18 and extends inside of outer sheath 17 along suture groove 34. Transducer assembly 20, shown in FIG. 1, may be activated to drive ultrasonic bone anchor 30 into bone mass 38.

Figure 6:
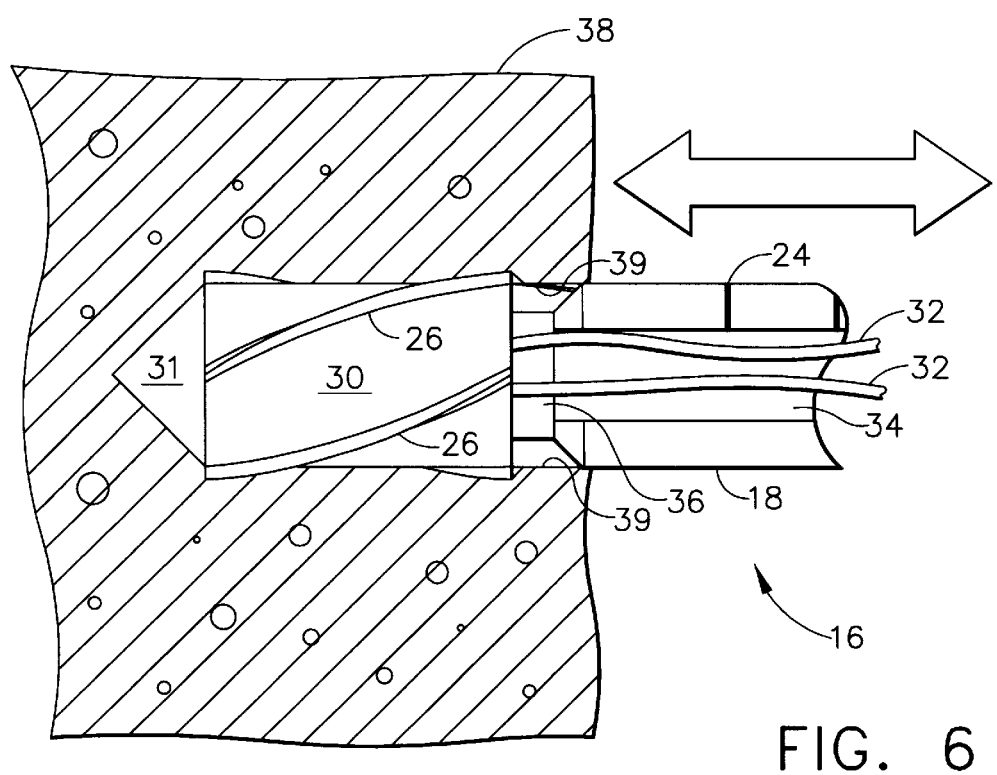
FIG. 6 is a fragmentary, partially sectioned view of an ultrasonic bone anchor being driven into bone by an ultrasonic waveguide.

FIG. 6 is a fragmentary, partially sectioned view of an ultrasonic bone anchor 30 being driven into bone mass 38 by ultrasonic insertion device 10 which is connected to ultrasonic bone anchor 30 by ultrasonic waveguide 18. Bone anchor tip 31 of ultrasonic bone anchor 30 will be driven into bone mass 38. As ultrasonic bone anchor 30 is driven into bone mass 38, creating anchor pilot hole 39, depth indicators 24 will indicate to the user the depth of bone anchor tip 31 as measured in, for example, millimeters. As ultrasonic bone anchor 30 is driven into bone mass 38 by ultrasonic embedding device 10, anchor thread 26 will rotate ultrasonic bone anchor 30 and waveguide assembly 16 in a counter-clockwise direction, as illustrated in FIG. 6. (Clockwise is defined herein as the rotation direction of the hands of a standard analog clock when viewing ultrasonic embedding device 10 while holding device housing 12 with the distal end of ultrasonic waveguide 18 pointed away from the observer.) Suture groove 34 will protect suture 32 from damage resulting from contact with the interior wall of anchor pilot hole 39 in bone mass 38.

Ultrasonic bone anchor 30 is driven into bone mass 38 using mechanical energy at ultrasonic frequency, creating anchor pilot hole 39. Bone anchor tip 31, when energized, vibrates reciprocally with a tip peak to peak excursion of, for example, about 100 micrometers. The bone anchor tip 31 of the ultrasonic embedding device 10 may have an excursion of between 50 and 300 micrometers, which would correspond to tip peak velocities ranging from 8.7 meters per second to 52.3 meters per second at 55,500 Hertz. The reciprocal motion will compact and fragment bone mass 38 and create anchor pilot hole 39 analogous to a jackhammer driving its tip into cement.

Anchor threads 26 of an ultrasonic bone anchor 30 are preferably no finer in pitch than one full turn per bone anchor length, and most preferably less than or equal to ¼ turn per bone anchor length. For example, a one centimeter long ultrasonic bone anchor 30 would preferably have no more than about one turn per centimeter thread pitch. Non-ultrasonic bone anchors utilize external threads to assist insertion of bone anchors into pre-drilled pilot holes. Finer thread pitches such as, for example, three to twenty threads per centimeter, require more turns of a non-ultrasonic bone anchor for a given insertion depth, but reduce insertion force as thread pitch becomes finer. Ultrasonic bone anchors utilize ultrasonic energy to reduce insertion force. External threads of ultrasonic bone anchors 30 are primarily utilized to restrict rotation of the bone anchor within anchor pilot hole 39 during removal of ultrasonic bone anchor 30 from ultrasonic embedding device 10. The preferable range for ultrasonic bone anchors 30 is zero to two turns per ultrasonic bone anchor 30 length. Finer pitches than two turns per ultrasonic bone anchor 30 length may actually be detrimental to ultrasonic bone anchor 30 purchase of bone mass 38 by causing an enlarging of bone anchor hole 39 during insertion.

In an alternate embodiment of the invention, rotation of waveguide assembly 16, as a result of the force applied by anchor thread 26 during embedding of ultrasonic bone anchor 30 into bone mass 38, may be used to indicate depth of embedding of ultrasonic bone anchor 30 into bone mass 38. Rotation knob 14 is rigidly connected to ultrasonic waveguide 18, and will rotate with respect to device housing 12 as waveguide assembly 16 rotates. Depth indicators 24 are spaced along the distal end of ultrasonic waveguide 18 to indicate how far ultrasonic bone anchor 30 has penetrated into bone during placement. Depth indicators may alternately be located in device housing 12, which utilize the rotation of waveguide assembly 16 or rotation knob 14 to indicate depth of embedding of ultrasonic bone anchor 30 into bone mass 38.

Figure 7:
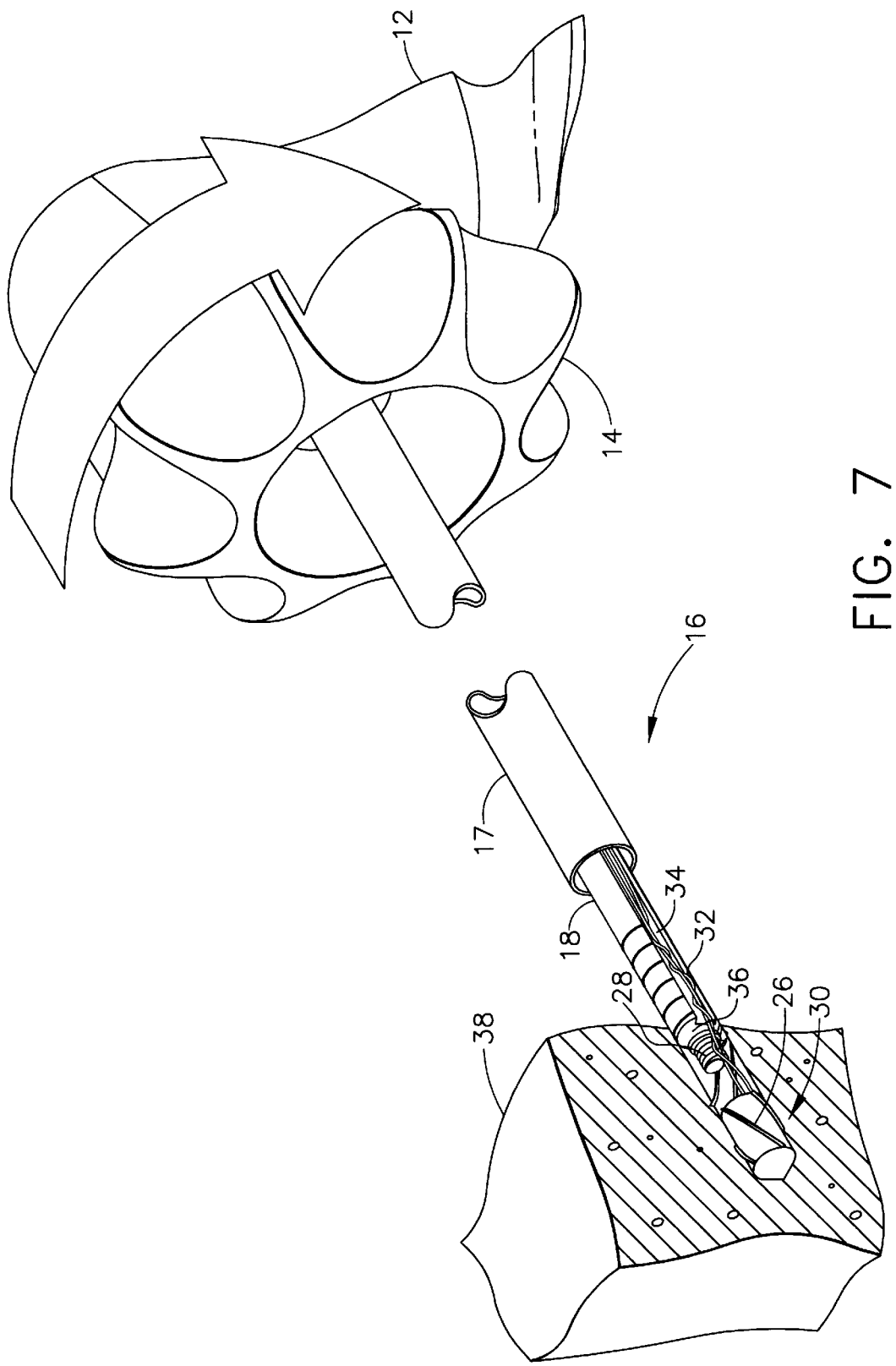
FIG. 7 is a fragmentary, perspective, partially sectioned view illustrating removal of the ultrasonic bone anchor from the ultrasonic bone anchor driver.

FIG. 7 is a fragmentary, perspective, partially sectioned view illustrating removal of ultrasonic bone anchor 30 from the ultrasonic embedding device 10. Removal of ultrasonic bone anchor 30 from waveguide assembly 16 may be accomplished by counter-clockwise rotation of rotation knob 14. Rotation knob 14 is rigidly fixed to both outer sheath 17 and ultrasonic waveguide 18, but is rotatably mounted to device housing 12 as described in U.S. patent application 08/948,952 previously incorporated herein by reference. Counter-clockwise torque applied to threaded connector 28 will unscrew waveguide stud 52 from anchor recess 58 while forcing ultrasonic bone anchor 30 into bone mass 38 due to the left hand pattern of anchor thread 26. Suture attachment waveguide recess 36 at the distal end of ultrasonic waveguide 18 will facilitate disengagement of ultrasonic bone anchor 30 from ultrasonic waveguide 18 without pinching or damaging suture 32. Suture 32 will be pulled along suture groove 34 of ultrasonic waveguide 18 as waveguide assembly 16 is removed from ultrasonic bone anchor 30.

Figure 8:
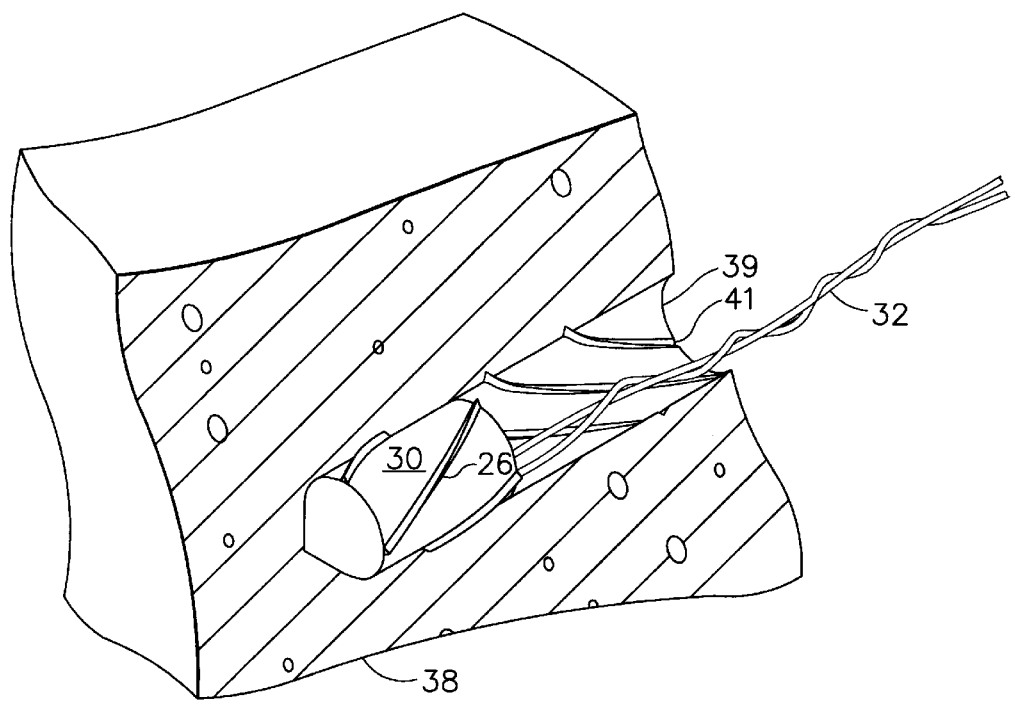
FIG. 8 is an enlarged partially sectioned isometric view of an ultrasonic bone anchor set in bone with suture extending out of the bone.

FIG. 8 is an enlarged partially sectioned isometric view of an ultrasonic bone anchor 30 set in bone mass 38 with suture 32 extending out of the bone mass 38. Ultrasonic bone anchor 30 is set in bone mass 38, and fixed in place by anchor thread 26. Suture 32 extends out of bone mass 38 and can be used for attachment to bone mass 38. Anchor pilot hole 39 has been formed in bone mass 38 by driving ultrasonic bone anchor 30 into bone mass 38 using ultrasonic embedding device 10. Thread track 41 is illustrated in bone mass 38 on the inner surface of anchor pilot hole 39.

Figure 9:
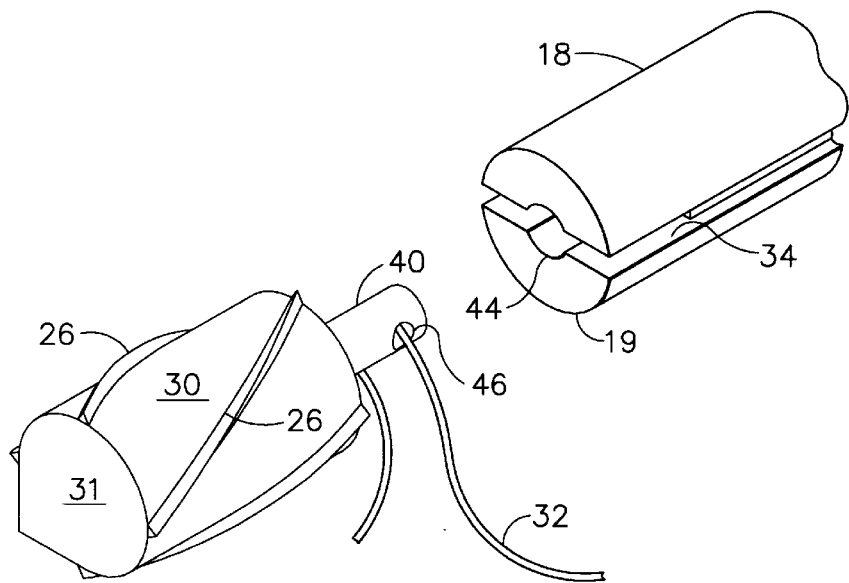
FIG. 9 is an enlarged fragmentary isometric view of an ultrasonic bone anchor driver distal end and an ultrasonic bone anchor, illustrating a taper connection between the ultrasonic bone anchor and ultrasonic bone anchor driver.

FIG. 9 is an enlarged fragmentary isometric view of another embodiment of ultrasonic bone anchor 30, illustrating a taper connection between ultrasonic bone anchor 30 and ultrasonic embedding device 10. Ultrasonic waveguide 18 of ultrasonic embedding device 10 is illustrated containing waveguide post recess 44, which is tapered as it extends into ultrasonic waveguide 18 from waveguide distal face 19. Ultrasonic bone anchor 30 contains suture attachment post 40 which is also tapered to fit into waveguide post recess 44. Suture attachment post 40 contains post suture opening 46 which accommodates insertion of suture 32 through post suture opening 46 of suture attachment post 40. Suture 32 may lie within suture groove 34 of ultrasonic waveguide 18 during embedding, or suture 32 may be inserted into post suture opening 46 of ultrasonic bone anchor 30 after ultrasonic bone anchor 30 has been driven into bone mass 38 (FIG. 8).

Figure 10:
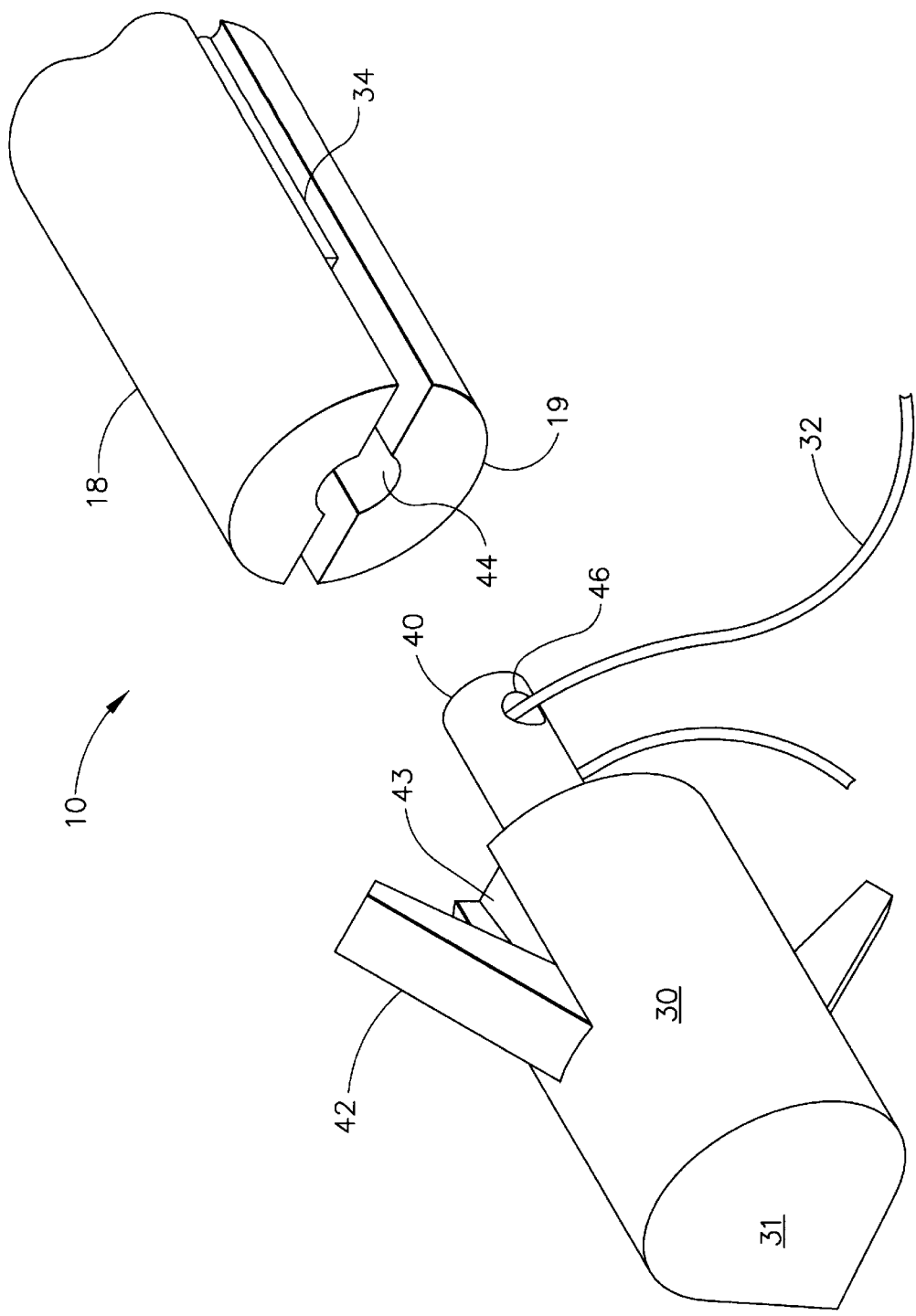
FIG. 10 is an enlarged fragmentary isometric view of an ultrasonic bone anchor driver distal end and an ultrasonic bone anchor containing barbs, illustrating a taper connection between the ultrasonic bone anchor and ultrasonic bone anchor driver.

FIG. 10 is an enlarged fragmentary isometric view of a bone anchor ultrasonic embedding device 10 distal end and an ultrasonic bone anchor 30 containing barbs 42, illustrating a taper connection between ultrasonic bone anchor 30 and ultrasonic embedding device 10. Referring to FIGS. 8 and 10, barbs 42 are used in place of the anchor thread 26 to anchor ultrasonic bone anchor 30 into bone mass 38. Barb 42 lies within anchor barb recess 43 of ultrasonic bone anchor 30 during embedding of ultrasonic bone anchor 30 into bone mass 38. Barb 42 may be manufactured from elastic material such that barb 42 pushes out against the inner surface of anchor pilot hole 39 after embedding of ultrasonic bone anchor 30 into bone mass 38, restricting ultrasonic bone anchor 30 from backing out of anchor pilot hole 39. Barbs 42 or anchor threads 26 will increase the purchase, or holding strength, of ultrasonic bone anchor 30 in anchor pilot hole 39.

Transducer assembly 20 (FIG. 1A), which may also be referred to as a handpiece, comprises an ultrasonic transducer, preferably a piezoceramic transducer, for converting an electrical signal, for example, a 55,500 Hz sinusoidal waveform, into a mechanical longitudinal vibration. A suitable ultrasonic transducer assembly is available from Ethicon Endo-Surgery, Inc. as make ULTRACISION® and model HP051.

Instrument device housing 12 includes rotation knob 14. Waveguide assembly 16 comprises outer sheath 17, ultrasonic waveguide 18, and ultrasonic bone anchor 30. Rotation knob 14 is rigidly connected to waveguide assembly 16. A surgeon using ultrasonic embedding device 10 may grasp device housing 12 in one hand, and rotate rotation knob 14 with either a finger, or the other hand. Rotation of rotation knob 14 causes waveguide assembly 16, ultrasonic bone anchor 30, and transducer assembly 20 to rotate within device housing 12.

Embedding of ultrasonic bone anchor 30 may be accomplished by bringing bone anchor tip 31 in contact with an area of bone mass 38 where a fastening location is desired. The surgeon will then cause transducer assembly 20 to be energized. Ultrasonic energy will propagate along ultrasonic waveguide 18 and be delivered through ultrasonic bone anchor 30 to bone anchor tip 31. Bone anchor tip 31 will be caused to vibrate longitudinally at an excursion of approximately 50 micrometers to 300 micrometers at an ultrasonic frequency of, for example, 55,500 Hertz. As the surgeon applies a small forward force to device housing 12, ultrasonic bone anchor 30 will penetrate bone mass 38 assisted by the ultrasonic embedding force.

Ultrasonic bone anchor 30 may be driven into bone mass 38 with or without the need for a pre-drilled hole. Ultrasonic bone anchor 30, having an excursion of between 50 and 300 micrometers, would correspond to bone anchor tip 31 peak accelerations ranging from about 480,000 meters per second$^2$ to 2,900,000 meters per second$^2$ at 55,500 Hertz. The force generated at bone anchor tip 31 to bone mass 38 due to the mass and acceleration of the bone anchor tip 31 greatly reduces the force required by the surgeon to accomplish the embedding.

Embedding of ultrasonic bone anchor 30 into bone mass 38 without a pre-drilled hole is best accomplished using an ultrasonic bone anchor 30 manufactured from a hard material such as, for example, Ti-6A1-4V, a titanium alloy. However, ultrasonic bone anchor 30 may also be manufactured from polymeric materials which are softer than bone.

Embedding of an ultrasonic bone anchor 30 manufactured from a polymeric material is best accomplished by pre-drilling the bone mass 38 with a hole slightly smaller than the diameter of ultrasonic bone anchor 30. As ultrasonic bone anchor 30 is driven into bone mass 38 using ultrasonic energy, ultrasonic bone anchor 30 will be swaged to an optimum size for the pre-drilled hole. This will result in a stronger anchor attachment than if the hole was the same size or larger than the ultrasonic bone anchor 30, as is described in the prior art. Embedding force by the surgeon to swag ultrasonic bone anchor 30 into bone mass 38 will be minimal due to the ultrasonic force assistance as described above.

Referring to FIGS. 1 and 1A, the acoustic assembly 50 of the ultrasonic embedding device 10 generally includes transducer stack 60 used to convert electrical energy into mechanical energy, velocity transformer 64 used to amplify excursion, ultrasonic waveguide 18 used to transfer the mechanical energy, and ultrasonic bone anchor 30. In order for the acoustic assembly 50 to deliver energy through the ultrasonic bone anchor 30, the transducer stack 60, ultrasonic waveguide 18, and ultrasonic bone anchor 30 must be acoustically coupled. The distal end of the transducer stack 60 is acoustically coupled to the proximal end of ultrasonic waveguide 18 preferably by a threaded connection.

The components of the acoustic assembly 50 are preferably acoustically tuned such that the length of each component is an integral number of one-half wavelengths ($n\lambda/2$), where the wavelength $\lambda$ is the wavelength of a pre-selected or operating longitudinal vibration frequency $f_0$ of the acoustic assembly 50, and where n is any positive integer. It is also contemplated that the acoustic assembly 50 may incorporate any suitable arrangement of acoustic elements.

The transducer assembly 20 of the acoustic assembly 50 converts the electrical signal from a signal generator into mechanical energy that results in longitudinal vibratory motion of the acoustic assembly 50 at ultrasonic frequencies. When the acoustic assembly 50 is energized, a vibratory motion standing wave is generated through the acoustic assembly 50. The excursion of the vibratory motion at any point along the acoustic assembly 50 depends on the location along the acoustic assembly 50 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength ($\lambda/4$).

As illustrated in FIGS. 3, 9 and 10, the ultrasonic waveguide 18 of the second acoustic portion is preferably detachably coupled to ultrasonic bone anchor 30. The ultrasonic waveguide 18, including ultrasonic bone anchor 30 acoustically coupled thereto, preferably has a length substantially equal to an integer number of one-half system wavelengths ($n\lambda/2$). The ultrasonic waveguide 18 is preferably fabricated from a solid core shaft constructed out of material which propagates ultrasonic energy efficiently, such as titanium alloy (i.e., Ti-6A1-4V) or an aluminum alloy. It is contemplated that the ultrasonic waveguide 18 can alternatively be fabricated from any other suitable material.

The ultrasonic waveguide 18 may be semi-flexible. The waveguide may be configured to amplify the mechanical vibrations transmitted through the waveguide to the end-effector as is well known in the art. The waveguide may further have features to control the gain of the longitudinal vibration along the waveguide and features to tune the waveguide to the resonant frequency of the system.

It is important to account for the acoustic property of ultrasonic bone anchor 30 in the ultrasonic embedding device 10. An ultrasonic bone anchor 30 manufactured from a material such as, for example, Ti-6A1-4V titanium alloy, acoustically couples to ultrasonic waveguide 18 to become part of the resonant acoustic system, having an overall length of $n\lambda/2$. If the acoustic length (the length as measured in wavelengths) of the bone anchor is, for example, $\lambda/16$, then the overall acoustic length of the ultrasonic embedding device 10 is optimally adjusted to $(n\lambda/2)-\lambda/16$.

Embedding devices of 5 mm diameter or less inherently begin to become more flexible as their diameters decrease. This flexibility causes them to buckle under compressive load as a surgeon attempts to embed a bone anchor. Utilizing a tuned acoustic assembly 50 in a standing wave mode of vibration allows the embedding of very small ( less than 5 mm ) ultrasonic bone anchors. As described earlier, ultrasonic waveguides have the ability to produce significant forces at the tip of ultrasonic bone anchor 30. The dynamic, resonant, standing wave nature of the ultrasonic tip force does not significantly contribute to the buckling load of the embedding device. This allows significant embedding force application without significant surgeon force application to the embedding device that could lead to embedding device buckling.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method of ultrasonically embedding bone anchors into bone, said method comprising the steps of:

a) providing a bone anchor, wherein said bone anchor comprises:

a proximal end including a coupling element;
a distal end;
an outer surface, including at least one protrusion on said outer surface of said body;
a central portion between said distal end and said proximal end, said central portion having a length, wherein said protrusion is a thread, said thread having a thread pitch less than one turn per said bone anchor central portion length;

b) providing an ultrasonic bone anchor embedding device, wherein said bone anchor is attachable to said bone anchor embedding device and wherein said bone anchor embedding device is adapted to transmit ultrasonic energy therethrough;

c) placing said bone anchor against a bone;

d) energizing said bone anchor embedding device causing said bone anchor embedding device to vibrate ultrasonically;

e) embedding said bone anchor into said bone; and f) removing said bone anchor embedding device from said bone anchor.

2. A method of embedding bone anchors into bone according to claim 1, wherein said bone anchor coupling element includes screw threads.

3. A method of embedding bone anchors into bone according to claim 2, comprising removing said bone anchor embedding device from said bone anchor with a counter clockwise rotation of said bone anchor embedding device.

4. A method of embedding bone anchors into bone, said method comprising the steps of:
a) providing a bone anchor, wherein said bone anchor comprises:
a body having a bone anchor body length and an outer surface;
a proximal end including a bone anchor coupling element; and
at least one engagement thread on said outer surface of said bone anchor
wherein said engagement thread is formed as a left-handed thread, said engagement thread having a thread pitch less than one turn per said bone anchor body length;

b) providing an ultrasonic bone anchor embedding device, wherein said bone anchor is attachable to said bone anchor embedding device and wherein said bone anchor embedding device is adapted to transmit ultrasonic energy therethrough;

c) placing said bone anchor against a bone;

d) energizing said bone anchor embedding device causing said bone anchor embedding device to vibrate ultrasonically;

e) embedding said bone anchor into said bone; and f) removing said bone anchor embedding device from said bone anchor.

5. A method of embedding bone anchors into bone according to claim 4 wherein said thread has a thread pitch of approximately one quarter turn per said bone anchor body length.

6. A method of embedding bone anchors into bone, said method comprising the steps of:
a) providing a bone anchor, wherein said bone anchor comprises:

a body including an outer surface;
a proximal end including a bone anchor coupling element; and
engagement threads on said outer surface of said bone anchor wherein said engagement threads are formed as left-handed threads;

b) providing a bone anchor embedding device wherein said bone anchor is attachable to said bone anchor embedding device and wherein said bone anchor embedding device is adapted to transmit ultrasonic energy therethrough;

c) drilling a pilot hole in a bone, said pilot hole having a hole diameter, wherein said hole diameter is less than or equal to said bone anchor diameter;

d) placing said bone anchor in contact with said pilot hole;

e) energizing said bone anchor embedding device causing said bone anchor embedding device to vibrate ultrasonically;

f) embedding said bone anchor into said pilot hole; and g) removing said bone anchor embedding device from said bone anchor.

7. A method of embedding bone anchors into bone according to claim 6, wherein said bone anchor coupling element includes screw threads formed as right-handed threads.

8. A method of embedding bone anchors into bone according to claim 7, comprising removing said bone anchor embedding device from said bone anchor with a counter clockwise rotation of said bone anchor embedding device.

9. A method of embedding bone anchors into bone, said method comprising the steps of:
a) providing a bone anchor, wherein said bone anchor comprises:
a body having a bone anchor body length and an outer surface;
a proximal end including a bone anchor coupling element; and
at least one engagement thread on said outer surface of said bone anchor wherein said engagement thread is formed as a left-handed thread, said engagement thread having a thread pitch less than one turn per said bone anchor body length;

b) providing a bone anchor embedding device wherein said bone anchor is attachable to said bone anchor embedding device and wherein said bone anchor embedding device is adapted to transmit ultrasonic energy therethrough;

c) drilling a pilot hole in a bone, said pilot hole having a hole diameter, wherein said hole diameter is less than or equal to said bone anchor diameter;

d) placing said bone anchor in contact with said pilot hole;

e) energizing said bone anchor embedding device causing said bone anchor embedding device to vibrate ultrasonically;

f) embedding said bone anchor into said pilot hole; and g) removing said bone anchor embedding device from said bone anchor, wherein said step of removing said bone anchor embedding device from said bone anchor sets said bone anchor into said bone.

10. A method of embedding bone anchors into bone according to claim 9 wherein said thread has a thread pitch of about one quarter turn per said bone anchor body length.

* * * * *